United States Patent [19]

Sernetz

[11] Patent Number: 5,383,784
[45] Date of Patent: Jan. 24, 1995

[54] AUZILIARY ORTHODONTIC APPLIANCE

[75] Inventor: Friedrich Sernetz, Pforzheim, Germany

[73] Assignee: Dentaurum J. P. Winkelstroeter KG, Ispringen, Germany

[21] Appl. No.: 108,732

[22] PCT Filed: Mar. 13, 1992

[86] PCT. No.: PCT/EP92/00559

§ 371 Date: Sep. 1, 1993

§ 102(e) Date: Sep. 1, 1993

[87] PCT Pub. No.: WO92/16159

PCT Pub. Date: Oct. 1, 1992

[30] Foreign Application Priority Data

Mar. 16, 1991 [DE] Germany ............................ 91104117

[51] Int. Cl.⁶ ................................................. A61C 3/00
[52] U.S. Cl. ............................................... 433/7; 433/8; 433/23
[58] Field of Search .................... 433/7, 8, 9, 10, 11, 433/12, 13, 14, 15, 16, 17, 23

[56] References Cited

U.S. PATENT DOCUMENTS

| | | | |
|---|---|---|---|
| 4,722,689 | 2/1988 | Corbett | 433/23 |
| 4,818,226 | 4/1989 | Berendt et al. | 433/20 |
| 5,066,224 | 11/1991 | Block et al. | 433/7 |
| 5,167,499 | 12/1992 | Arndt et al. | 433/7 |

FOREIGN PATENT DOCUMENTS 0297908 1/1989 European Pat. Off. .
2318617 2/1977 France .

Primary Examiner—Gene Mancene
Assistant Examiner—Nicholas D. Lucchesi
Attorney, Agent, or Firm—Edward J. Timmer

[57] ABSTRACT

Auxiliary orthodontic appliance, namely expansion screw for the maxilla or mandible, bracket or buccal tube, which in order to improve its properties consists of titanium or an alloy on the basis of titanium and the surfaces of which are formed by a titanium oxide skin.

10 Claims, 1 Drawing Sheet

AUZILIARY ORTHODONTIC APPLIANCE

BACKGROUND OF THE INVENTION

The invention relates to an auxiliary orthodontic appliance for human beings. This may be an auxiliary orthodontic or orthopaedic appliance for the maxilla or mandible. As used in technical terminology, such an auxiliary appliance is an article in the form of an expansion screw, a bracket, a buccal tube or a ring-shaped tooth band which remains in the mouth for a limited amount of time. Expansion screws are used for expanding the human jaw and also for correcting the position of one or several teeth. Brackets and buccal tubes also serve to correct the position of the teeth and are attached to the teeth, in the given circumstances, by means of a ring-shaped band which surrounds the pertinent tooth.

An expansion screw usually consists of two screw body parts and a threaded spindle which has threads running in opposite directions on either side of a spindle head at the center of the threaded spindle and engages corresponding threaded bores of the two screw body parts so that the two screw body parts are adjustable relative to one another by turning the threaded spindle. In the given circumstances, guide means, in particular, in the form of guide pins, can also be provided to prevent the two screw body parts from twisting in opposite directions when the threaded spindle is turned. The various parts of expansion screws known so far consist of stainless steel or nickel-silver alloys. Stainless steel was also used for the manufacture of brackets and buccal tubes, but ceramic and plastic brackets are also known, however, these are not fully satisfactory with respect to their strength.

Although it has been known for a long time that stainless steel and nickel-silver are not sufficiently resistant to corrosion for these purposes and, in particular, can cause allergic reactions on account of their nickel content, so far not a single manufacturer of such auxiliary appliances anywhere in the world has marketed expansion screws, brackets or buccal tubes which do not have the disadvantages explained above.

As the auxiliary appliances in question are worn in the mouth, the prevention of electrochemical corrosion of the auxiliary appliance constitutes quite a considerable problem. For example, in view of amalgam tooth fillings, the metallic auxiliary appliances known so far have also not proven fully satisfactory in this respect. In the case of expansion screws made of nickel-silver with guide pins and threaded spindles made of stainless steel, for example, the electrochemical corrosion can occur within a few days if the parts made of nickel-silver are not protected by a chrome or nickel coating.

SUMMARY OF THE INVENTION

The object underlying the invention was to create auxiliary appliances of the kind in question which do not lead to problems even if the wearer has already undergone restorative dental treatment, and in accordance with the invention this object is accomplished by the auxiliary appliance consisting of titanium or an alloy on the basis of titanium and its surfaces being formed by a titanium oxide skin whose electrical breakdown potential in synthetic saliva with a pH value of 2.3 at 37° C. is greater than 2000 mV.

Titanium and titanium alloys have been in use for a long time for high-quality technical parts such as, for example, watch cases, and owing to their biocompatibility also as materials for implants. However, in spite of the difficulties indicated hereinabove and known for a long time, so far expansion screws, brackets and buccal tubes have never been made of titanium or alloys on the basis of titanium anywhere in the world. These auxiliary orthodontic appliances are distinct mass-produced articles in the manufacture of which these materials have not gained access although titanium and its alloys can be worked in an absolutely economical way by the available cutting tools, titanium and its alloys are obtainable as fine powders so the auxiliarly appliances an question can also be manufactured economically by metal injection molds, and although molding materials are available to allow titanium and its alloys to also be castable economically in a precision casting process.

Surprisingly it was ascertained that a titanium oxide skin as defined hereinabove passivates the inventive auxiliary appliances to be worn in the mouth sufficiently even if the wearer also has teeth which are provided with an artificial part consisting of an alloy with a high gold content, which can be added as a further advantage to the known biocompatibility of titanium and alloys on the basis of titanium.

To measure the breakdown potential of the oxide skin which is producible, for example, by anodic oxidation or annealing in an atmosphere containing oxygen, synthetic saliva according to German Industrial Standard 13912 and a measuring cell according to ASTM (see G5-Rec. Practice for Standard Reference Method for making Potentiostatic and Potentiodynamic Anodic Polarisation Measurements, 1980 Annual Book of ASTM Standard, Part 10) should be used; in this connection reference is also made to the essay "Grundsätzliches zur Methodik potentiodynamischer Polarisationsmessungen an Dentallegierungen in küstlichen Speicheln" (Basics on the method of potentiodynamic polarisation measurements of dental alloys in artificial salivas) by J. Geis-Gerstorfer and H. Weber, Deutsche Zahnärztliche Zeitschrift (German dentists' magazine) 42, 1987, pages 91–97.

Alloys on the basis of titanium are to be understood as high-alloy titanium alloys according to German Industrial Standard 17851.

A particular advantage of the inventive measure is obtained with expansion screws in which higher demands have to be made on the strength of the threaded spindle than on that of the screw body parts. In known expansion screws with a threaded spindle made of a material of higher strength than the screw body parts, the galvanic corrosion of the parts made of nickel-silver could only be reduced by coating them with nickel or chrome. With an inventive expansion screw, on the other hand, the respectively required strength of screw body parts and threaded spindle is achieved solely by the choice of different, standardized degrees of purity of the titanium without this causing differences in the electrochemical series (titanium is available on the market in four different standardized degrees of purity according to German Industrial Standard 17850—grades 1 to 4—which differ in their strength, more particularly, titanium of a lower degree of purity has a greater strength than purer titanium and so, for example, grade 4 titanium is used for the threaded spindle of an expansion screw according to the invention, whereas, for example, grade 1 or 2 titanium can be used for the screw body parts. Nevertheless, there is never any allergy risk with an expansion screw according to the invention, which is not the case with the known expansion screws made of stainless steel or of nickel-silver with a nickel coating.

BRIEF DESCRIPTION OF THE DRAWINGS

Three embodiments of the auxiliary appliance according to the invention are shown in perspective illustrations in the appended drawings, more particularly, in FIG. 1: an expansion screw, in
FIG. 2: a bracket and in
FIG. 3: a buccal tube.

DESCRIPTION OF THE INVENTION

Figure 1:
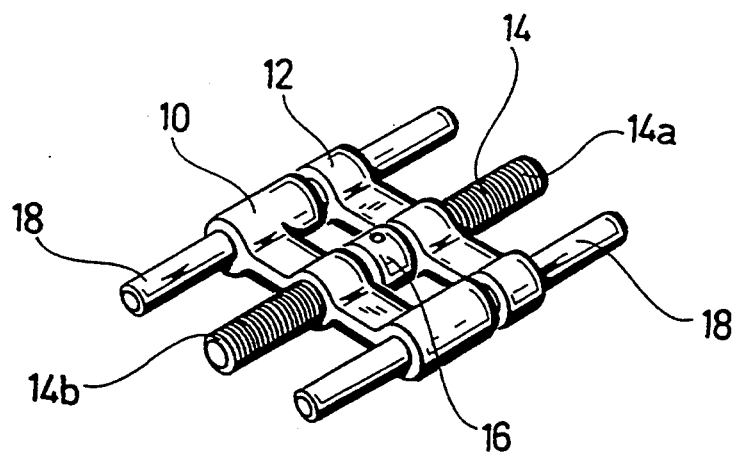

The expansion screw shown in FIG. 1 consists of a first and a second screw body part 10 and 12, respectively, a threaded spindle 14 with a spindle head 16 and two guide pins 18. The threaded spindle 14 has on either side of the spindle head 16 spindle sections 14a and 14b with threads running in opposite directions. These engage corresponding threaded bores of the screw body parts 10 and 12 so that the spacing of the two screw body parts 10, 12 from one another is adjustable by turning the threaded spindle 14. The two guide pins 18 can each be fixed in one of the two screw body parts 10, 12 as they are primarily to prevent the two screw body parts 10, 12 from twisting in opposite directions when the threaded spindle 14 is turned. A transverse bore 16a in the spindle head 16 enables insertion of a tool for actuation of the threaded spindle 14.

As mentioned previously, the threaded spindle 14 can consist, for example, of grade 4 titanium, whereas the remaining parts of the expansion screw for maxilla or mandible can consist of grade 1, 2 or 3 titanium, and all of the surfaces of the various parts are coated with a thin titanium oxide skin.

Figure 2:
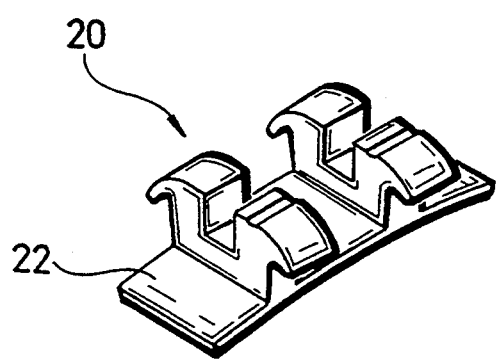
Figure 3:
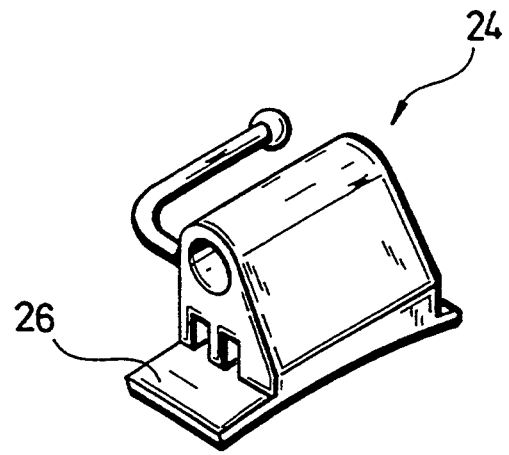

FIG. 2 shows a bracket designated in its entirety 20 with a base 22, FIG. 3 a buccal tube designated in its entirety 24 with a base 26 which like the base 22 of the bracket 20 for attaching the bracket to a tooth, serves to attach the buccal tube to a tooth. Neither the bracket nor the buccal tube requires further description as the design of these auxiliary appliances is known and the latter differ from the known auxiliary appliances only in the material and in the feature that their surfaces are coated with a thin titanium oxide skin.

When an alloy on the basis of titanium is referred to hereinabove, this means that this alloy contains more than 50 per cent by weight titanium. The oxide skin can be readily obtained in an oxidizing atmosphere, and the thickness of the oxide coating can be controlled by, for example, changing the composition of the oxidizing atmosphere, the treatment temperature and/or the duration of the treatment—a relatively thick oxide coating can be produced even by a short heating of the auxiliary appliances in air without having to accept a loss in the strength of the parts.

I claim:

1. Auxiliary orthodontic appliance, characterized in that said auxiliary appliance comprises at least one of titanium and an alloy on the basis of titanium and its surfaces are formed by a titanium oxide skin whose electrical breakdown potential in synthetic saliva with a pH value of 2.3 at 37° C. is greater than 2000 mV.

2. Auxiliary appliance as defined in claim 1 comprising two screw body parts adjustable relative to one another by means of a threaded spindle, characterized in that said threaded spindle consists of a titanium material of higher strength than said screw body parts.

3. Auxiliary appliance as defined in claim 2, characterized in that said threaded spindle consists of titanium of a lower purity than said screw body parts.

4. Auxiliary appliance as defined in claim 1, characterized in that its components are in the form of injection molded parts.

5. Auxiliary appliance as defined in claims 1, characterized in that its components are in the form of precision castings.

6. Auxiliary orthodontic appliance, characterized in that said auxiliary appliance comprises at least one of titanium and an alloy on the basis of titanium and its surfaces are formed by a passivating skin comprising a compound of titanium formed in-situ on the surfaces and having an electrical breakdown potential in synthetic saliva with a pH value of 2.3 at 37° C. greater than 2000 mV.

7. Auxiliary appliance as defined in claim 6 comprising two screw body parts adjustable relative to one another by means of a threaded spindle, characterized in that said threaded spindle consists of a titanium material of higher strength than said screw body parts.

8. Auxiliary appliance as defined in claim 6, characterized in that said threaded spindle consists of titanium of a lower purity than said screw body parts.

9. Auxiliary appliance as defined in claim 6, characterized in that its components are in the form of injection molded parts.

10. Auxiliary appliance as defined in claim 6, characterized in that its components are in the form of precision castings.

* * * * *

UNITED STATES PATENT AND TRADEMARK OFFICE
CERTIFICATE OF CORRECTION

PATENT NO.　：　5 383 784
DATED　　　：　January 24, 1995
INVENTOR(S)：　Friedrich SERNETZ It is certified that error appears in the above-indentified patent and that said Letters Patent is hereby corrected as shown below:

On the title page, item [54],
　　　In the title, replace　"AUZILIARY"　with ——AUXILIARY——.

Signed and Sealed this

Fourteenth Day of November, 1995

Attest:

BRUCE LEHMAN

*Attesting Officer*　　　*Commissioner of Patents and Trademarks*